(12) United States Patent
Browning et al.

(10) Patent No.: US 8,128,822 B2
(45) Date of Patent: Mar. 6, 2012

(54) MECS DIALYZER

(75) Inventors: David M. Browning, Portland, OR (US);
James R. Curtis, Portland, OR (US);
Goran Nadezda Jovanovic, Corvallis, OR (US); Brian Kevin Paul, Corvallis, OR (US); Sundar Atre, Corvallis, OR (US)

(73) Assignees: State of Oregon acting by and through The State Board of Higher Education on behalf of Oregon State University, Corvallis, OR (US); Home Dialysis Plus, Portland, OR (US)

( * ) Notice: Subject to any disclaimer, the term of this patent is extended or adjusted under 35 U.S.C. 154(b) by 627 days.

(21) Appl. No.: 11/576,804

(22) PCT Filed: Oct. 6, 2005

(86) PCT No.: PCT/US2005/036095
§ 371 (c)(1),
(2), (4) Date: Nov. 1, 2007

(87) PCT Pub. No.: WO2006/042079
PCT Pub. Date: Apr. 20, 2006

(65) Prior Publication Data
US 2008/0093298 A1    Apr. 24, 2008

Related U.S. Application Data

(60) Provisional application No. 60/616,757, filed on Oct. 6, 2004.

(51) Int. Cl.
*B01D 61/28* (2006.01)
*B01D 61/24* (2006.01)

(52) U.S. Cl. ............... 210/321.71; 210/646; 210/321.75

(58) Field of Classification Search .................. None
See application file for complete search history.

(56) References Cited

U.S. PATENT DOCUMENTS 3,695,445 A    10/1972    Esmond
(Continued)

FOREIGN PATENT DOCUMENTS

JP    S55-14045    1/1980
(Continued)

OTHER PUBLICATIONS

Australian patent application No. 2005294236 (National Stage of instant application)—Examiner's First Report dated Dec. 4, 2009.

(Continued)

*Primary Examiner* — Krishnan S Menon
(74) *Attorney, Agent, or Firm* — Silicon Forest Patent Group; Paul J Fordenbacher, Esq.

(57) ABSTRACT

The present invention is related to hemodialysis, and more particularly, to a dialyser with improved efficiency of mass transfer across a dialysis membrane utilizing microchannel separation provided in accordance with embodiments of the present invention. In accordance with an embodiment, a dialyzer is provided comprising a plurality of semipermeable membrane sheets and a plurality of flow separators. The membrane sheets and flow are arranged in alternating configuration and coupled into a laminae stack defining a plurality of parallel microchannel layers. Each microchannel layer comprises a plurality of first microchannels and a plurality of second microchannels. The first and second microchannels of each microchannel layer are in fluid communication with each other via one of the plurality of membrane sheets therebetween. The MECS dialyzer is characterized as having a high surface to volume ratio and a high mass transfer coefficient.

18 Claims, 9 Drawing Sheets

U.S. PATENT DOCUMENTS

| | | | |
|---|---|---|---|
| 3,827,563 A | 8/1974 | Boe et al. | |
| 4,110,220 A | 8/1978 | Lavender | |
| 4,310,416 A | 1/1982 | Tanaka et al. | |
| 4,476,022 A * | 10/1984 | Doll | 210/321.83 |
| 4,500,426 A * | 2/1985 | Ishii et al. | 210/321.73 |
| 4,624,784 A | 11/1986 | Lefebvre | |
| 4,756,835 A * | 7/1988 | Wilson | 210/651 |
| 5,316,676 A | 5/1994 | Drori | |
| 5,593,581 A | 1/1997 | Lescoche | |
| 5,611,214 A | 3/1997 | Wegeng et al. | |
| 5,811,062 A | 9/1998 | Wegeng et al. | |
| 5,868,930 A | 2/1999 | Kopf | |
| 6,123,798 A | 9/2000 | Gandhi et al. | |
| 6,126,723 A | 10/2000 | Drost et al. | |
| 6,129,973 A | 10/2000 | Martin et al. | |
| 6,192,596 B1 | 2/2001 | Bennett et al. | |
| 6,352,577 B1 | 3/2002 | Martin et al. | |
| 6,368,505 B1 | 4/2002 | Grummert et al. | |
| 6,375,871 B1 | 4/2002 | Bentsen et al. | |
| 6,454,942 B1 * | 9/2002 | Shintani et al. | 210/321.74 |
| 6,490,812 B1 | 12/2002 | Bennett et al. | |
| 6,514,412 B1 | 2/2003 | Insley et al. | |
| 6,533,840 B2 | 3/2003 | Martin et al. | |
| 6,607,644 B1 | 8/2003 | Apffel, Jr. | |
| 6,635,226 B1 | 10/2003 | Tso et al. | |
| 6,666,909 B1 | 12/2003 | TeGrotenhuis et al. | |
| 6,672,502 B1 | 1/2004 | Paul et al. | |
| 6,688,381 B2 | 2/2004 | Pence et al. | |
| 6,749,814 B1 | 6/2004 | Bergh et al. | |
| 6,793,831 B1 | 9/2004 | Paul et al. | |
| 6,797,056 B2 | 9/2004 | David | |
| 6,986,428 B2 | 1/2006 | Hester et al. | |
| 6,989,134 B2 | 1/2006 | Tonkovich et al. | |
| 6,994,829 B2 | 2/2006 | Whyatt et al. | |
| 7,014,705 B2 | 3/2006 | David | |
| 7,094,345 B2 | 8/2006 | Gilbert et al. | |
| 7,097,800 B2 | 8/2006 | Vigna et al. | |
| 7,125,540 B1 | 10/2006 | Wegeng et al. | |
| 7,264,723 B2 | 9/2007 | Singh et al. | |
| 7,279,134 B2 | 10/2007 | Chan et al. | |
| 7,316,780 B1 * | 1/2008 | Fendya et al. | 210/510.1 |
| 7,501,101 B2 | 3/2009 | Wegeng et al. | |
| 7,507,380 B2 | 3/2009 | Chang et al. | |
| 7,534,315 B1 | 5/2009 | Singh et al. | |
| 2002/0162784 A1 * | 11/2002 | Kohlheb et al. | 210/321.6 |
| 2003/0039169 A1 | 2/2003 | Ehrfeld et al. | |
| 2003/0052429 A1 * | 3/2003 | Vigna et al. | 264/45.1 |
| 2004/0084370 A1 | 5/2004 | Singh et al. | |
| 2005/0145497 A1 | 7/2005 | Gilbert et al. | |
| 2006/0266692 A1 | 11/2006 | Foster et al. | |
| 2007/0029365 A1 | 2/2007 | Paul et al. | |
| 2007/0119771 A1 | 5/2007 | Schukar et al. | |
| 2008/0009780 A1 | 1/2008 | Leonard et al. | |

FOREIGN PATENT DOCUMENTS

| | | |
|---|---|---|
| JP | S59-58002 | 10/1982 |
| WO | WO02076529 A1 | 10/2002 |

OTHER PUBLICATIONS

European patent application No. 05810241.9 (National Stage of instant application)—Extended European search report dated May 6, 2009.

Japanese patent application No. 2007-535829 (National Stage of instant application)—Notice of Rejection dated Dec. 1, 2009.

Japanese patent application No. 2007-535829 (National Stage of instant application)—Final Notice of Rejection dated Jul. 1, 2010.

Chinese patent application No. 200580041446.8 (National Stage of instant application)—First Office Action dated Feb. 20, 2009.

* cited by examiner

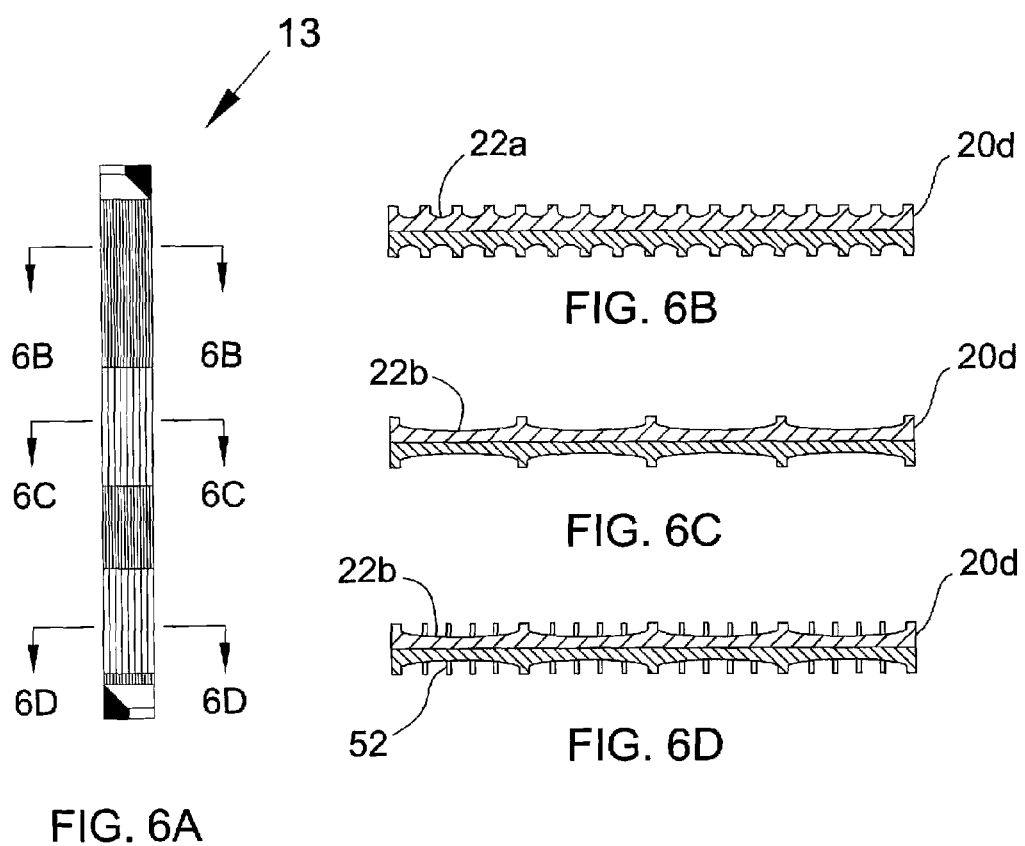

MECS DIALYZER

RELATED APPLICATIONS

This is a non-provisional application claiming benefit under 35 USC §119(e) to Provisional application No. 60/616,757, filed on Oct. 6, 2004, which is in its entirety incorporated herewith by reference

FIELD OF THE INVENTION

The present invention is related to hemodialysis, and more particularly, to methods and apparatus for a microtechnology-based dialyzer.

BACKGROUND

Chronic dialysis has been performed on patients with kidney failure since the early 1960's. The dialyzers or "artificial kidneys" that made this possible were a result of a technical evolution that began in the 1930's and 1940's. A dialyzer is a device for cleansing blood through hemodialysis by a process of diffusion and convection of waste products, dissolved solutes and fluid from the blood across a semi-permeable membrane into a dialysis solution known as dialysate. A dialyzer system is an assembly comprising the dialyzer and associated equipment to support the dialyzer, such as plumbing and pumps.

The first dialyzer systems used were made of a large rotating drum that used sausage casing as a semi-permeable membrane wrapped over a large round, wooden frame. Blood was routed through the casing and the casing was bathed in dialysate solution. By the 1970's the industry had developed the hollow fiber dialyzer. This device is made of 10,000-14,000 hollow semi-permeable membrane fibers housed in a tube 30 cm long and 6 cm in diameter, yet providing up to two square meters of surface area for blood flowing within the fibers to interface with dialysate flowing around the outside of the fibers. Though the hollow fiber dialyzers of today are a bit more efficient, the technology has not changed significantly since this time.

The hollow fiber dialyzer has a mal-distribution of dialysate flow due to uneven and inconsistent spacing between individual fibers. Areas with stagnant flow as well as areas with developed shunt flow dramatically reduce the efficiency of the mass transfer on the dialysate side. The spacing between individual fibers is generally small, thus diffusion is an important mechanism of mass transfer in the inter-fiber space. Improvement of diffusion, and hence improved dialysate usage efficiency is limited due to the inherent physical character of the hollow-fiber dialyzers.

Currently, hollow fiber dialyzers use 120-200 liters of dialysate solution, comprising predominantly water, to perform a dialysis treatment. A relatively large quantity of dialysate solution is used because the flow of dialysate is haphazard around the fibers. The need for this quantity of dialysate solution requires that dialysis machine be quite large. The water used for dialysis must also be purified of chemical and microbiological contamination which adds to the amount of equipment and the technical expertise needed to perform dialysis treatments.

As a result of the reliance on this complicated equipment, most dialysis treatments are performed at dialysis centers staffed by a team of professionals. Less than one percent of hemodialysis patients perform their own treatments at home. In a center, dialysis treatments are performed in a very rapid manner over a short period of time. Each patient receives three treatments per week. Studies have shown that there is a great improvement when patients are dialyzed slower, longer, and more often. Not only are the patient outcomes much better, the overall cost of their care is less due to reductions in medication and hospitalization costs.

The only economically viable way for patients to receive more frequent dialysis treatments is for them to perform their own dialysis treatments at home. To make this technically feasible it is necessary to improve the technology such that dialysis machines are smaller, more portable, consume less water, and be simpler for the lay person to operate.

What is needed in the art is a dialyzer with improved efficiency of mass transfer across the dialysis membrane that separates the blood from the dialysate solution.

BRIEF DESCRIPTION OF THE DRAWINGS

Like reference numbers generally indicate corresponding elements in the figures.

FIG. 6A is a top view of a MECS dialyzer having microchannels of a plurality of aspect ratios, in accordance with an embodiment of the present invention;

FIG. 6B is a cross-sectional view of the MECS dialyzer of the embodiment of FIG. 6A about cut plane 6B-6B showing that at this section, the microchannel sheet comprises relatively low aspect ratio grooves;

FIG. 6C is a cross-sectional view of the MECS dialyzer of the embodiment of FIG. 6A about cut plane 6C-6C showing that at this section, the microchannel sheet comprises relatively high aspect ratio grooves;

FIG. 6D is a cross-sectional view of the MECS dialyzer of the embodiment of FIG. 6A about cut plane 6D-6D showing that at this section, the microchannel sheet comprises relatively high aspect ratio grooves further comprising support webs adapted to further support the membrane across the groove and resulting flow channel;

SUMMARY OF THE INVENTION

Figure 1:
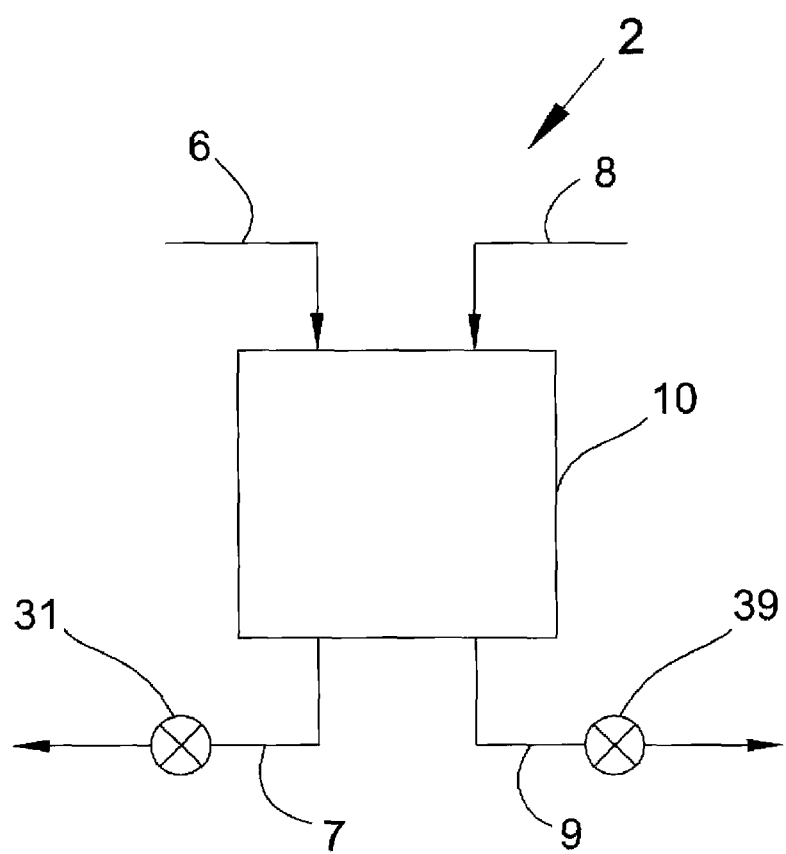
FIG. 1 is a schematic of a dialysis system in accordance with the present invention.

The present invention is related to hemodialysis, and more particularly, to a dialyzer with improved efficiency of mass transfer across a dialysis membrane utilizing microchannel separation provided in accordance with embodiments of the present invention. In accordance with an embodiment, a dialyzer is provided comprising a plurality of semipermeable membrane sheets and a plurality of flow separators. The membrane sheets and flow separators are arranged in alternating configuration and coupled into a laminae stack defining a plurality of parallel microchannel layers. Each microchannel layer comprises a plurality of first microchannels and a plurality of second microchannels. The first and second microchannels of each microchannel layer are in fluid communication with each other via one of the plurality of membrane sheets therebetween.

In an embodiment, the first microchannels of each microchannel layer are parallel and the second microchannels of each microchannel layer are parallel.

In an embodiment, the first and second microchannels of the microchannel layers are parallel.

In an embodiment, the first and second microchannels of the microchannel layers are orthogonal.

In an embodiment, the flow separators comprise a plurality of first microchannel sheets and second microchannel sheets. The first microchannel sheets have a first side and a second side opposite the first side, the second side having parallel grooves therein. The second microchannel sheets have a first side and a second side opposite the first side, the first and second sides having parallel grooves therein. The laminae stack has a laminae stack top side and a laminae stack bottom side. Each microchannel layer comprises a laminae sub-stack comprising either a first and second microchannel sheet with a membrane sheet therebetween and coupled therewith, the grooves in facing relationship separated by the membrane sheet at the laminae stack top and bottom sides, or two second microchannel sheets with a membrane sheet therebetween and coupled therewith, the grooves in facing relationship separated by the membrane sheet.

In an embodiment, the flow separators comprise a plurality of first and second microchannel sheets. The first microchannel sheets have a first side and a second side opposite the first side, and a first end and a second end opposite the first end, with at least one side having parallel grooves extending from the first end to the second end. The second microchannel sheets have a first side and a second side opposite the first side, and a first end and a second end opposite the first end, at least one side having parallel grooves extending from the first end to the second end. Each microchannel layer comprises a laminae sub-stack comprising a first and second microchannel sheet with a membrane sheet therebetween and coupled therewith, the grooves in facing relationship separated by the membrane sheet.

In an embodiment, the plurality of first microchannel sheets further comprise a first plena groove at each of the first and second ends. The first plena groove is in fluid communication with the grooves on the first microchannel sheets. The plurality of second microchannel sheets further comprise a second plena groove at each of the first and second ends, the second plena groove in fluid communication with the grooves on the second microchannel sheets.

In accordance with an embodiment, a dialyzer is provided comprising a plurality of semipermeable membrane sheets and a plurality of flow separators. The membrane sheets and flow separators are arranged in alternating configuration and coupled into a laminae stack defining a plurality of parallel microchannel layers. Each microchannel layer comprises a plurality of first microchannels and a plurality of second microchannels. The first and second microchannels of each microchannel layer are in fluid communication with each other via one of the plurality of membrane sheets therebetween. Each membrane sheet has a first side and a second side opposite the first side, and a first end and a second end opposite the first end. The flow separators depend from the first and second sides defining parallel grooves extending from the first end to the second end. Each microchannel layer comprises a unit laminae stack comprising at least two membrane sheets, the grooves in facing relationship and the flow separators adjacent each other and coupled therewith defining alternating layers of first and second microchannels.

In an embodiment, the dialyzer comprises a first header and a second header. The first header comprises an inlet in fluid communication with the first microchannels at the first end and an outlet in fluid communication with the second microchannels at the first end. The second header comprises an inlet in fluid communication with the second microchannels at the second end and an outlet in fluid communication with the first microchannels at the second end.

In an embodiment, the dialyzer comprises a first header and a second header. The first header comprises an inlet in fluid communication with the first microchannels at the first end and an inlet in fluid communication with the second microchannels at the first end. The second header comprises an outlet in fluid communication with the first microchannels at the second end and an outlet in fluid communication with the second microchannels at the second end.

In accordance with an embodiment, a dialyzer system is provided comprising a blood-handling apparatus, dialysate-handling apparatus, and a dialyzer. The dialyzer comprises a plurality of semipermeable membrane sheets and a plurality of flow separators. The membrane sheets and flow separators are arranged in alternating configuration and coupled into a laminae stack defining a plurality of parallel microchannel layers. Each microchannel layer comprises a plurality of first microchannels and a plurality of second microchannels. The first and second microchannels of each microchannel layer are in fluid communication with each other via one of the plurality of membrane sheets therebetween. The blood-handling apparatus is in fluid communication with the first microchannels and the dialysate-handling apparatus is in fluid communication with the second microchannels.

In an embodiment, the blood-handling apparatus is adapted to supply blood to the first microchannels at a first end and withdraw blood from the second microchannels at a second end. The dialysate-handling apparatus is adapted to supply dialysate to the second microchannels at a second end and withdraw dialysate from the second microchannels at a first end.

In an embodiment, the blood-handling apparatus is adapted to supply blood to the first microchannels at a first end and withdraw blood from the second microchannels at a second end. The dialysate-handling apparatus is adapted to supply dialysate to the second microchannels at a first end and withdraw dialysate from the second microchannels at a second end.

In an embodiment, each membrane sheet has a first side and a second side opposite the first side, and a first end and a second end opposite the first end. The flow separators depend from the first and second sides defining parallel grooves extending from the first end to the second end. Each microchannel layer comprises a stack comprising at least three membrane sheets, the grooves in facing relationship and the flow separators adjacent each other and coupled therewith defining alternating layers of first and second microchannels.

In accordance with an embodiment, a method for dialysis of blood comprises providing a dialyzer having a plurality of semipermeable membrane sheets and a plurality of flow separators. The membrane sheets and flow separators are arranged in alternating configuration and coupled into a laminae stack defining a plurality of parallel microchannel layers. Each microchannel layer comprises a plurality of first microchannels and a plurality of second microchannels. The first and second microchannels of each microchannel layer are in fluid communication with each other via one of the plurality of membrane sheets therebetween. The blood-handling apparatus is in fluid communication with the first microchannels, the dialysate-handling apparatus in fluid communication with the second microchannels. The method further comprising supplying the first microchannels with blood at a first end, supplying the second microchannels with dialysate at a second end, withdrawing blood from the first microchannels at a second end, and withdrawing dialysate from the second microchannels at a first end.

Dialyzers made in accordance with the present invention provide embedded highly-parallel or perpendicular arrays of microchannels capable of accelerating the mass transfer in dialysis applications. Small characteristic sizes provided by the microchannels provide the benefits of large surface-to-volume ratios, laminar flow conditions and the opportunity of operating at elevated pressures.

Extremely high rates of mass transfer are obtainable in microchannels. The MECS dialyzer which incorporates microchannel geometry and micro-lamination manufacturing technologies radically reduces the characteristic or residence time required for mass transfer in a dialysis application. The microtechnology-based design maintains micro-scale dimensions evenly on both sides of the membrane. In an embodiment in accordance with the present invention, a microtechnology-based MECS dialyzer is provided with dialysate flow channel dimensions of 100 microns. Compared to a conventional dialyzer with hollow fibers, this geometry reduces the size of a dialyzer by a factor of 10 to 100 for the same operating parameters.

A major benefit of the MECS dialyzer in accordance with the present invention is the ability to optimize the dialysate flow so as to approach 100% utilization. The MECS dialyzer in accordance with embodiments of the present invention, uses a structured flow of dialysate through fixed-width microchannels. The spacing of the microchannels is predetermined for effective utilization of the dialysate used to clean the blood. Less dialysate solute reduces the dialysis machine size.

Additionally, the structured flow path minimizes areas of stagnant flow, eliminates shunt flows, and ensures maximum utilization of all areas of membrane exposed to the dialysate flow. This greatly improves solute clearance and allows for the dialyzer to have less surface area for a given performance requirement as compared with currently available hollow fiber dialyzers. The reduced membrane length and surface area reduces the pressure on the blood leading to a reduction in hemolysis and reduction in the amount of blood within the circuit that is outside the patient during treatment.

DETAILED DESCRIPTION

Reference will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

The term "microchannel" refers to a channel having at least one internal dimension of width or height of up to about 1000 microns.

The term "non-turbulent" refers to the flow of a fluid through a microchannel that is laminar or in transition. The Reynolds Number for the flow of the fluid through the microchannel may be up to about 4000. The Reynolds Number used herein is calculated using the hydraulic diameter which is based on the actual shape of the microchannel.

The term "MECS" refers to Microtechnology-based Energy and Chemical Systems and the methods of fabricating MECS devices, as provided in the International Application published under the Patent Cooperation Treaty (PCT) number WO 2005/045894 A2, High Volume Microlamination Production of Devices, which is incorporated herein by reference for all purposes.

The semi-permeable membrane, also referred to as membrane, may be any membrane suitable for use in diffusion dialysis, such as, but not limited to, porous polysulfone and those membranes disclosed in U.S. Pat. No. 6,258,276, Mika et al., incorporated herein by reference for all purposes.

The dialysate may be any dialysate solution suitable for use in hemodialysis.

The term "residence time", which may be referred to as "average residence time," is that time wherein diffusion takes place between the blood and dialysate through the membrane within the MECS dialyzer.

The present invention provides an ultra-small dialyzer based on MECS technology. The MECS dialyzer is a device for cleansing blood through hemodialysis by the process of diffusion and convection of solutes and excess liquid across a semi-permeable membrane into dialysate.

FIG. 1 is a schematic of a dialysis system 2 in accordance with the present invention. Blood is caused to flow through blood inlet line 6 to one or more first microchannels in the MECS dialyzer 10 and exits through blood outlet line 7 and blood valve 31. Dialysate is caused to flow through dialysate inlet line 8 to one or more second microchannels in the MECS dialyzer 10 and exits through dialysate outlet line 9 and dialysate valve 32. The first microchannels and the second microchannels are separated from each other by the membrane.

In the MECS dialyzer 10, solute and excess fluid is diffused from blood flowing through the first microchannels, through the membrane, and into dialysate flowing through the second microchannels. The MECS dialyzer contains a plurality of microchannel layers corresponding to the first and second microchannels bisected by membrane. The microchannel layers may be aligned one above the other in any desired sequence, as will be describe below.

Figure 2:
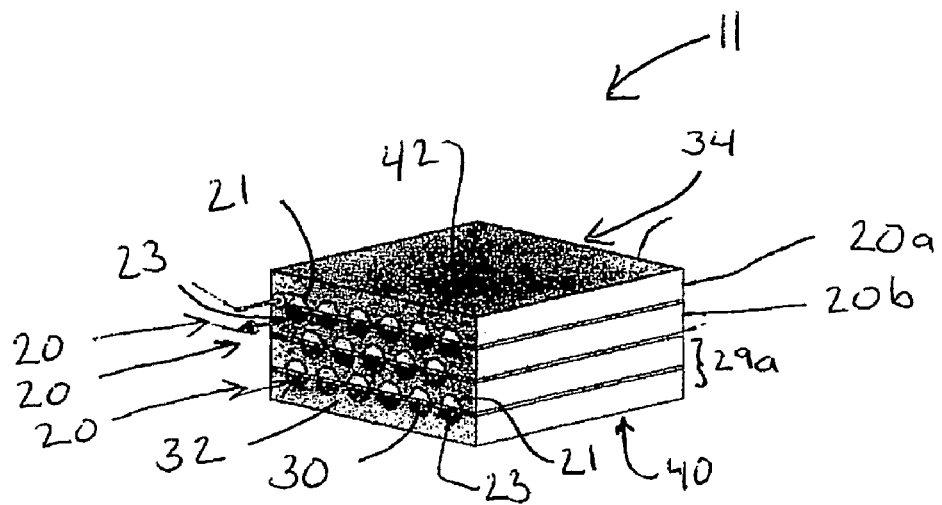
FIG. 2 is a perspective view of a parallel flow MECS dialyzer in accordance with an embodiment of the present invention.

FIG. 2 is a perspective view of a parallel flow MECS dialyzer 11 in accordance with an embodiment of the present invention. The MECS dialyzer 11 comprises a plurality of microchannel layers 20 located one above the other to defining a repeating unit 29a of microchannel layers 20. The microchannel layers 20 comprise a plurality of first microchannels 21 provided for the flow of blood and second microchannels 23 provided for the flow of dialysate. The first and second microchannels 21, 23 are defined by the membrane 30 therebetween and by microchannel flow separators as described below. The first and second microchannels 21, 23 are in fluid communication via the membrane 30.

The number of first microchannels 21 in each of the microchannel layers 20 may be any desired number, for example, tens, hundreds, thousands with a correspondingly same number of second microchannels 23. Similarly, the number of repeating units 29a of microchannel layers 20 may be any desired number, for example, tens, hundreds, thousands.

The first microchannels 21 of each microchannel layer 20 are arranged parallel and extend along the length of microchannel layer 20 from a first end 32 to a second end 34 opposite from the first end 32. The second microchannels 23 of each microchannel layer 20 are also arranged parallel and extend along the length of the microchannel layer 20 from the first end 32 to the second end 34.

In a method in accordance with an embodiment of the present invention including the MECS dialyzer 11, the blood is caused to flow through the first microchannels 21 from the first end 32 to the second end 34 and the dialysate is caused to flow through the second microchannels 23 from the second end 34 to the first end 32, that is, the flow is in opposite direction, referred to as countercurrent flow. Countercurrent flow improves the diffusion characteristics between the blood and dialysate through the membrane 30 and minimizes the amount of membrane surface area needed for waste clearance and minimizes dialysate quantity requirements.

In another method in accordance with an embodiment of the present invention including the MECS dialyzer 11, blood is caused to flow through the first microchannels 21 from the first end 32 to the second end 34 and the dialysate is caused to flow through the second microchannels 23 from the first end 32.to the second end 34, that is, the flow is in the same direction, referred to as concurrent flow.

Figure 3:
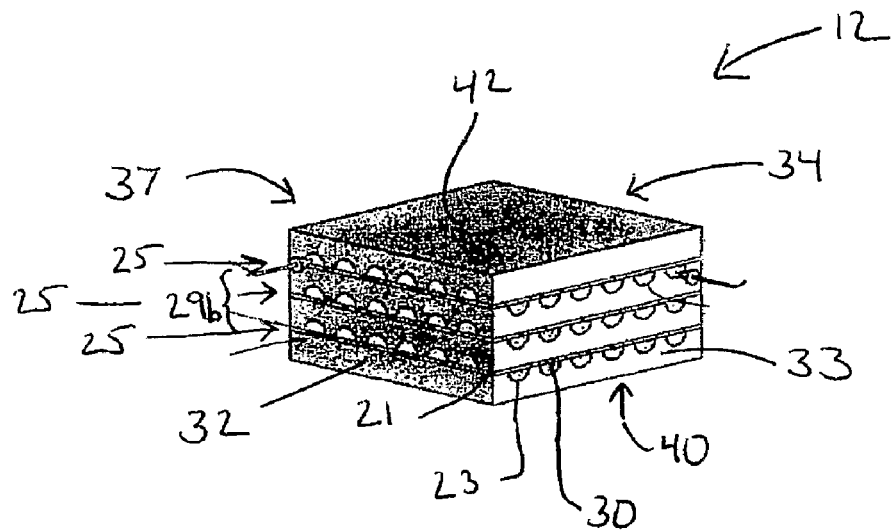
FIG. 3 is a perspective view of a cross-flow MECS dialyzer in accordance with an embodiment of the present invention.

FIG. 3 is a perspective view of a cross-flow MECS dialyzer 12 in accordance with an embodiment of the present invention. The MECS dialyzer 12 comprises a plurality of microchannel layers 25 located one above the other defining a repeating unit 29b of microchannel layers 25. The microchannel layers 25 comprise a plurality of first microchannels 21 provided for the flow of blood and second microchannels 23 provided for the flow of dialysate. The first and second microchannels 21, 23 are defined by the membrane 30 therebetween and by microchannel flow separators as described below. The first and second microchannels 21, 23 are in fluid communication via the membrane 30.

The first microchannels 21 of each microchannel layer 25 are arranged parallel and extend along the length of microchannel layer 25 from a first end 32 to a second end 34 defining a first direction. The second microchannels 23 of each microchannel layer 25 are also arranged parallel and extend along the length of the microchannel layer 25 from a third end 33 to a fourth end 37 opposite the third end 33 defining a second direction. The first and second directions are orthogonal to each other, and therefore the first microchannels 21 and the second microchannels 23 are orthogonal to each other.

In a method in accordance with an embodiment of the present invention including the MECS dialyzer 12, blood is caused to flow through the first microchannels 21 from the first end 32 to the second end 34 and the dialysate is caused to flow through the second microchannels 23 from the third end 33 to the fourth end 37, referred to as crosscurrent flow.

Similarly as with the embodiment of FIG. 2, the number of first microchannels 21 in each of the microchannel layers 25 may be any desired number, for example, tens, hundreds, thousands, with a correspondingly same number of second microchannels 23. Similarly, the number of repeating units 29b of microchannel layers 25 may be any desired number, for example, tens, hundreds, thousands.

In accordance with embodiments of the present invention, a number of methods are provided for the fabrication of microchannel layers 20, 25 comprising microchannels 21, 23 separated by membrane.

Figure 4:
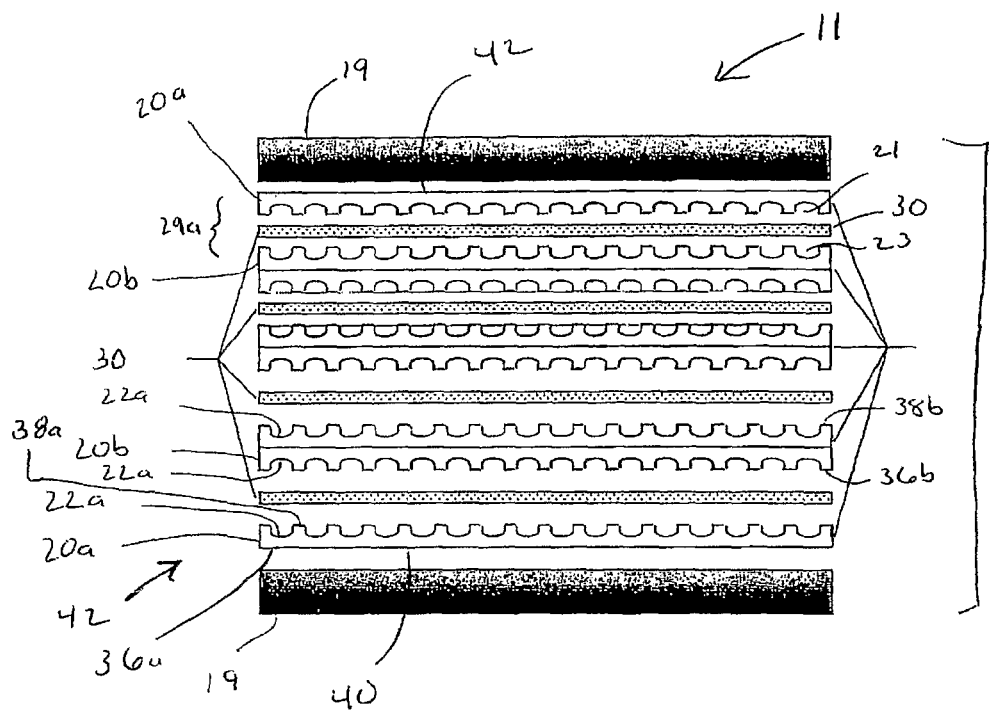
FIG. 4 is an exploded end view of a laminae stack including a plurality of first microchannel sheets, second microchannel sheets, and membrane sheets in a stacked arrangement, in accordance with an embodiment of the present invention.

Referring again to FIG. 2 and to FIG. 4 which is an exploded end view of the MECS dialyzer 11, the MECS dialyzer 11 comprises a laminae stack including a plurality of first microchannel sheets 20a, second microchannel sheets 20b, and membrane sheets 30 in a stacked arrangement, in accordance with an embodiment of the present invention. The first microchannel sheets 20a have a first side 36a and a second side 38a opposite the first side. The first side 36a is relatively smooth and the second side 38a comprises a plurality of grooves 22a. The grooves 22a are arranged in parallel and extend along the length of first microchannel sheets 20a from the first end 32 to the second end 34.

The second microchannel sheets 20b have a first side 36b and a second side 38b, both of which comprises a plurality of grooves 22a. The grooves 22a are arranged parallel and extend along the length of first microchannel sheets 20b from the first end 32 to the second end 34.

When the first and second microchannel sheets 20a,b are stacked, the grooves 22a are adapted to define and form parallel flow channels. In the embodiment of FIGS. 2 and 4, pairs of grooves 22a on different microchannel sheets 20a,b are adapted to align parallel to and be in fluid communication with each other. In the embodiment of FIG. 3, pairs of grooves 22a on different microchannel sheets 20a,b are adapted to cross over orthogonally and be in partial fluid communication with each other.

In the embodiment of FIG. 4, a first microchannel sheet 20a is provided on a top 42 and a bottom 40 of the MECS dialyzer 11. A plurality of second microchannel sheets 20b are provided between the first microchannel sheets 20a. The first and second microchannel sheets 20a, 20b are interleaved with a sheet of membrane, which bisects the intersection of the grooves 22a on different microchannel sheets 20a,b to define first and second microchannels 21, 23. The laminae stack is coupled or coupled in any one of suitable known processes and further described below.

Figure 5:
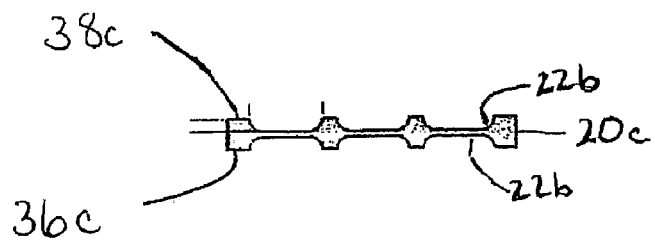
FIG. 5 is an end view of a third microchannel sheet having a first side and a second side opposite the first side comprising a plurality of grooves of an aspect ratio of about 5, in accordance with an embodiment of the present invention.

The grooves 22a of the first and second microchannel sheets 20a,b of the embodiment of FIG. 4 are shown to have an aspect ratio, that is, a width to height ratio, of about 2. The aspect ratio of the grooves in the microchannel sheets is predetermined for a particular purpose. FIG. 5 is an end view of a third microchannel sheet 20c having a first side 36c and a second side 38c opposite the first side comprising a plurality of grooves 22b of an aspect ratio of about 5, in accordance with an embodiment of the present invention. Higher aspect ratio grooves provide increased surface area of the membrane 30 between the first and second microchannels 21, 23, suitable for a particular purpose.

The microchannel sheet can be fabricated from a number of different materials as long as the material has the property of hemocompatibility. Examples if materials include polymers such as polysulfone. Additionally the microchannel sheet material must have material properties that allow it to be molded, micro machined, embossed, pattern printed, or micro fluidically sprayed onto the membrane surface, depending on the manufacturing process to be used to form grooves 22a,b.

Manufacturing options for the production of grooves 22a,b in microchannel sheets 20, 25 are known and include, among others: embossing, micromachining, deposition, silicon microfabrication techniques, laser ablimation with a Nd:YAG micromachining laser system, stamping, powder injection molding or otherwise forming or molding a microchannel sheet, electrochemical micromachining, photolithography, and soft lithography techniques and combinations thereof.

The laminae structure of the embodiments of the MECS dialyzer 11, 12 of FIGS. 2-4 allows for the mixing of different aspect ratios of the grooves either from microchannel layer to microchannel layer or from one end to the other end, suitable for a particular purpose.

FIG. 6A is a top view of a MECS 13 dialyzer having microchannels of a plurality of aspect ratios, in accordance with an embodiment of the present invention. FIG. 6B is an end view of a microchannel sheet 20d at the cut plane 6B-6B of the MECS dialyzer 13 showing that at this section, the microchannel sheet 20d comprises relatively low aspect ratio grooves 22a. FIG. 6C is an end view of a microchannel sheet 20d at the cut plane 6C-6C of the MECS dialyzer 13 showing that at this section, the microchannel sheet 20d comprises relatively high aspect ratio grooves 22b. FIG. 6D is an end view of a microchannel sheet 20d at the cut plane 6D-6D of the MECS dialyzer 13 showing that at this section, the microchannel sheet 20d comprises relatively high aspect ratio grooves 22b further comprising support webs 52 adapted to support the membrane (not shown) across the groove 22b and resulting flow channel.

The laminae structure of the embodiments of the MECS dialyzer of FIG. 2-4, 6 also allows for the integration of micro-plena or micro-manifolds to be incorporated in the microchannel sheets. The micro-plena provide for the distribution of blood and dialysate into respective microchannels from a single inlet port for each of the blood and dialysate.

Figure 7:
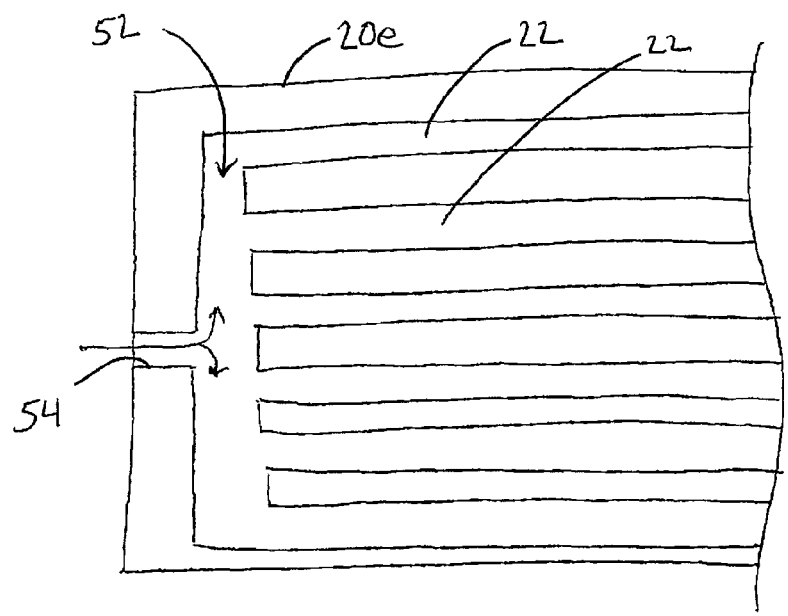
FIG. 7 is a top view of a microchannel sheet comprising a plurality of grooves, a plena groove in fluid communication with the grooves, and an inlet in fluid communication with the plena groove, in accordance with an embodiment of the present invention.

FIG. 7 is a top view of a microchannel sheet 20e comprising a plurality of grooves 22, a plena groove 52 in fluid communication with the grooves 22 and an inlet 54 in fluid communication with the plena groove 52, in accordance with an embodiment of the present invention. The plena groove 52 directs the incoming fluid from the inlet 54 to the plurality of grooves 22. A similar arrangement may be provided at a second end of the microchannel sheet 20e to provide a plena for an outlet for the fluid exiting the grooves 22 as will be described below.

Figure 8A:
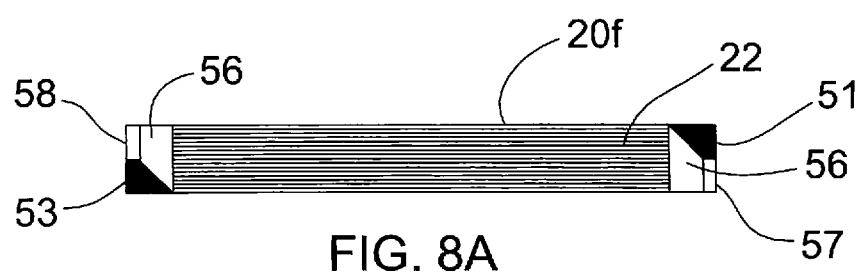
FIGS. 8A and 8B are top views of two microchannel sheets comprising a plurality of grooves, two plena grooves in fluid communication with the grooves at either a first and second end, and an inlet and an outlet in fluid communication with either of the plena grooves, in accordance with an embodiment of the present invention.
Figure 8B:
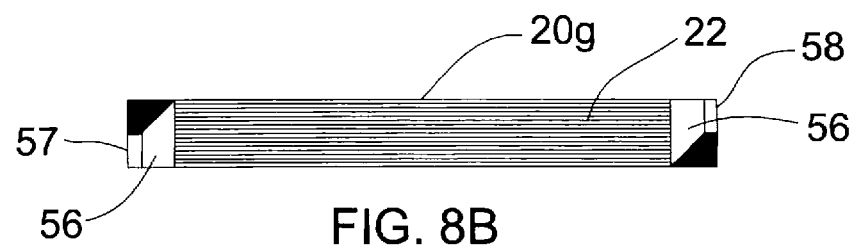
Figure 8C:
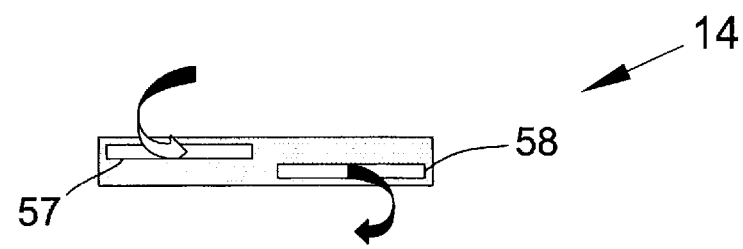
FIG. 8C is an end view of a MECS dialyzer made in accordance with the microchannel sheets of the embodiment of FIGS. 8A and 8B.

FIGS. 8A and 8B are top views of microchannel sheets 20f, 20g comprising a plurality of grooves 22, two plena grooves 56 in fluid communication with the grooves 22, one at a first and second end 51, 53, and an inlet 57 and an outlet 58 in fluid communication with one or the other of the plena grooves 56, in accordance with an embodiment of the present invention. The plena grooves 56 direct the incoming or outgoing fluid from the inlet 54 or outlet 58 to/from the plurality of grooves 22. FIG. 8C is an end view of a MECS dialyzer 14 made in accordance with the microchannel sheets 20f, 20g showing the inlet 57 and the outlet 58 of a coupled stack of microchannel sheets 20f, 20g.

The laminae structure of the embodiments of the MECS dialyzer allows for successive microchannel sheets to be rotated ninety-degrees with respect to adjacent microchannel sheets so as to form two sets of orthogonally extending microchannels which are arranged in a cross-flow configuration as shown in FIG. 3.

The laminae stack can be coupled or bonded together using various methods. These bonding methods include, but not limited to: adhesive bonding; the bonding surfaces coated with bonding material, and the stack subjected to a thermal reflow process; ultrasonic welding, radio frequency welding, pressure bonding, diffusion bonding, bonding materials added to the membrane or microchannel sheet material, among others.

In an embodiment of a method in accordance with the present invention, the temperature of the laminae is elevated to soften and/or selectively melt a component of the laminae stack to bond the adjacent surfaces.

A particularly promising thermal bonding method uses a thermal expansion bonding fixture wherein the bonding fixture and the laminae is used to self-align the laminae in the fixture with a so called thermal-enhanced edge registration (TEER) method as described in the patent application published under the Patent Cooperation Treaty (PCT) number WO 2005/045894 A2, High Volume Microlamination Production of Devices, which is incorporated herein by reference for all purposes.

Figure 9B:
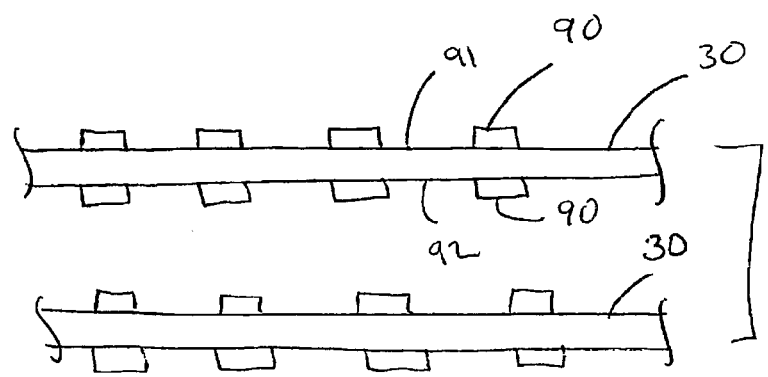
FIGS. 9B and 9C are exploded end and top views, respectively, of the MECS dialyzer of the embodiment of FIG. 9A.
Figure 9A:
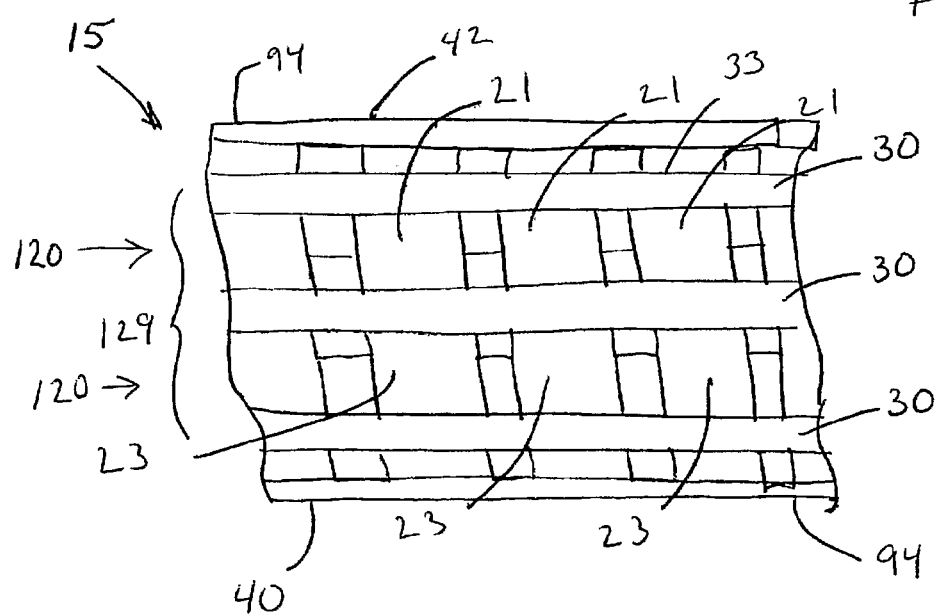
FIG. 9A is an end view of a parallel flow MECS dialyzer in accordance with an embodiment of the present invention.
Figure 9C:
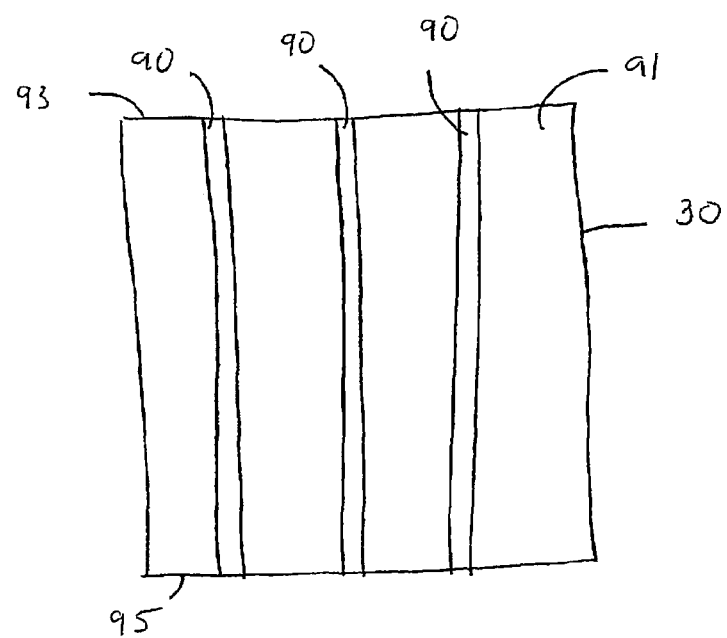

FIG. 9A is an end view of a parallel flow MECS dialyzer 15 in accordance with an embodiment of the present invention. The MECS dialyzer 15 comprises a plurality of membrane sheets 30 having a first side 91 and a second side 92. The membrane sheets 30 further comprise a plurality of flow separators 90 depending from the first and second sides 91, 92 in a predetermined pattern. FIG. 9B is an exploded end view of two membrane sheets 30 with flow separators 90 of the MECS dialyzer 16 of the embodiment of FIG. 9A. FIG. 9C is a top view of a membrane sheet 30 with flow separators 90 of the MECS dialyzer 15 of the embodiment of FIG. 9A. The flow separators 90 are arranged parallel and extend along the length of the membrane sheet 30 from a first end 93 to a second end 95 opposite from the first end 93. The flow separators 90 are adapted to intersect when two adjacent membrane sheets 90 are placed in a laminae stack.

Membrane sheets 30 with flow separators 90 are stacked one above the other to provide a repeating unit 129 of microchannel layers 120. The flow separators 90 and the membrane sheet 30 define a plurality of parallel first and second microchannels 21, 23. The MECS dialyzer 15 further comprises an end sheet 94 on the top 42 and bottom 40 of the stack to enclose and fluidically seal the adjacent flow separators 90.

The microchannel layers 120 comprise a plurality of first microchannels 21 provided for the flow of blood and second microchannels 23 provided for the flow of dialysate. The first and second microchannels 21, 23 are defined by the membrane 30 therebetween and by microchannel flow separators 90. The first and second microchannels 21, 23 are in fluid communication via the membrane 30. During consolidation of the laminae stack, the flow separators 90 bond together to form a fluid-tight seal using any suitable method including, but not limited to, reflow bonding and adhesive bonding.

In the embodiment of FIGS. 9A-C, each first microchannel 21 is in fluid communication with two second microchannels 23 via the membrane 30, except for those adjacent the end sheets 94, and therefore, provides about twice the membrane surface area as for the embodiments of FIGS. 2-4 for substantially similar sized first microchannels 21.

The flow separators 90 may be provided on the membrane 30 in a number of known processes suitable for the particular purpose. In embodiments in accordance with the present invention, the flow separators 90 are provided on the membrane using methods, such as, but not limited to, jet printing, silk screen printing, insitu bonding, and vapor deposition.

Figure 10:
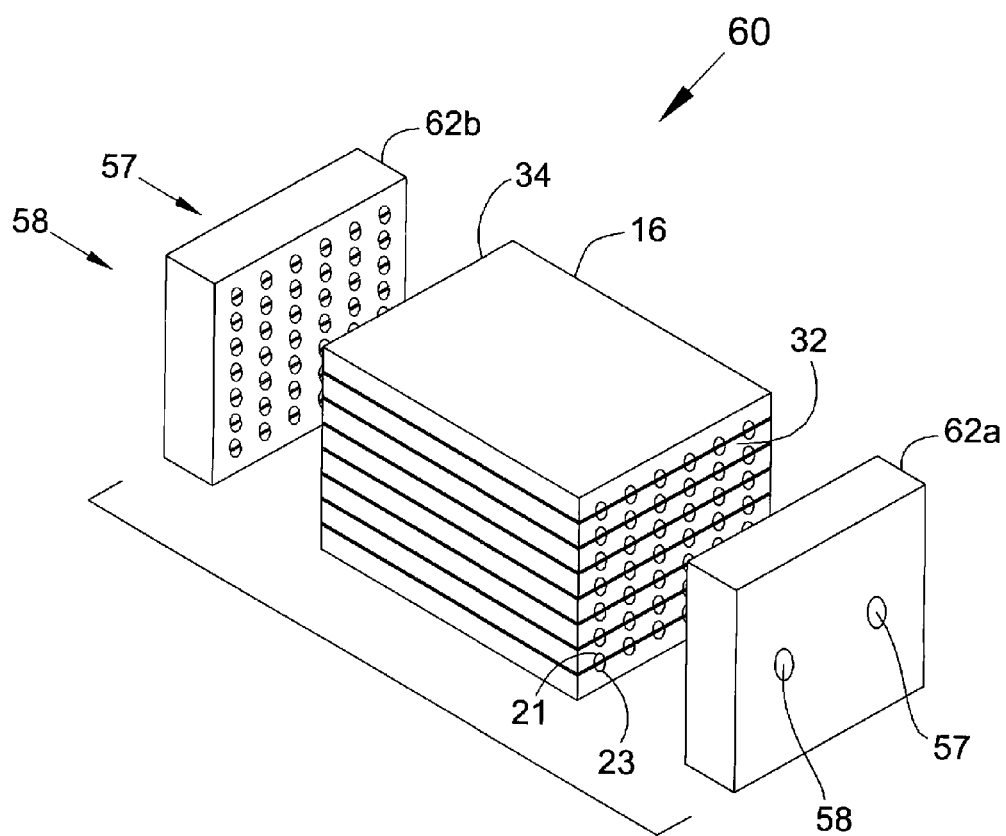
FIG. 10 is an exploded perspective view of a MECS dialyzer comprising a stack of microchannel sheets and two headers, in accordance with embodiments of the present invention.

FIG. 10 is an exploded perspective view of a MECS dialyzer unit 60 comprising a MECS dialyzer 16 and two headers 62a,b, in accordance with an embodiment of the present invention. Each of the two headers 62a,b comprise an inlet 57, an outlet 58 and channels for collecting blood and dialysate and distributing these fluids to the appropriate microchannels 21,23 of the MECS dialyzer 16. The first header 62a is adapted to receive blood from an extracorporeal blood line, distribute the blood to first microchannels 21 of the MECS dialyzer 16 as a laminar flow to minimize shear within the blood stream. The flow field within the first header 62a is controlled to minimize damage to blood cells as they travel through the first header 62a to the MECS dialyzer 16. The blood is then collected from the microchannels 21 in the second header 62b as it leaves the MECS dialyzer 16. The collected blood is then transferred by an extracorporeal blood line to be returned to the patient. The second header 62b includes features to reduce shear in the blood exit flow field which reduces damage to exiting blood cells.

In similar arrangement, the second header 62b is adapted to receive dialysate from a dialysate handling system and distribute it to the second microchannels 23 of the MECS dialyzer 16. The dialysate is then collected from the second microchannels 23 by the first header 62a as it leaves the MECS dialyzer 16. The collected dialysate is then transferred to a dialysate handling system. This configuration provides countercurrent flow between the blood and dialysate.

In a concurrent flow configuration between the blood and dialysate, the first header 62a is adapted to receive dialysate from a dialysate handling system and distribute it to the second microchannels 23 of the MECS dialyzer 16. The dialysate is then collected from the second microchannels 23 by the second header 62b as it leaves the MECS dialyzer 16. The collected dialysate is then transferred to a dialysate handling system.

In an embodiment of a MECS dialyzer unit, the headers incorporate a compliant interface and seal provided between the MECS dialyzer and the headers. The seal allows the MECS dialyzer and the headers to be coupled in fluid communication without requiring highly accurate manufacturing accuracies.

Each of the first microchannels 21 may have a cross section having any shape, such as, but not limited to, a square, rectangle or half-circle. Each of the first microchannels 21 may have an internal height or width of up to about 1000 microns, and in an embodiment the height is about 100 microns and the width is about 200 microns. The length of each first microchannel 21 may be up to about 0.5 cm.

In the embodiments of the MECS dialyzer 11, 12, the flow of blood through the first microchannels 21 may be laminar, in transition, or turbulent. In one embodiment, the flow of blood is laminar with the Reynolds Number for the blood through the first microchannels 21 of less than about 3000. In another embodiment, the flow is laminar or in transition with the Reynolds Number for the blood through the first microchannels 21 of less than about 4000. In another embodiment, flow is turbulent with the Reynolds Number for the blood through the first microchannels 21 greater than about 4000. It is understood that blood is a non-Newtonian fluid, that is, non-homogeneous, so the concept of Reynolds Number as it applies to blood is used assuming that blood is a Newtonian fluid of a predetermined viscosity. Due to the vulnerability of some blood constituents, for example blood cells and platelets, to damage and/or the initiation of the clotting cascade, to high shear stresses that may be encountered in turbulent flow, laminar flow properties are desired and attainable in the MECS dialysis in accordance with embodiments of the present invention.

The flow of dialysate through the second microchannels 23 may be laminar, in transition, or turbulent. Each of the second microchannels 23 may have a cross section having any shape, such as, but not limited to, a square, rectangle or half-circle. Each of the second microchannels 23 may have an internal height or width of up to about 1000 microns, and in an embodiment the height is about 100 microns and the width is about 200 microns. The length of each first microchannel 23 may be any suitable length predetermined for a particular purpose, such as, but not limited to, dialysate utilization as a function of residence time per length. In one embodiment, the flow is laminar with the Reynolds Number for the dialysate through the second microchannels 23 less than about 3000. In another embodiment, the flow is laminar or in transition with the Reynolds Number for the dialysate through the second microchannels 23 less than about 4000. In another embodiment, flow is turbulent with the Reynolds Number for the dialysate through the second microchannels 23 greater than about 4000.

The membrane material currently used in most hollow fiber dialyzer designs is polysulfone. The porosity is controlled at the time of manufacture but there are limitations on the construction methods. The flat sheet membranes used in the MECS dialyzer allow many improvements in membrane design. Design improvements include layering of the membrane with nanostructures to support stiffer, thinner membrane for reducing dialyzer compliance during pulsatile flow conditions as well as more permeable membranes for improved hemodialysis and hemocompatibility. This composite structure provides the ability to embed nano particles to enhance the membrane performance including targeting specific solutes for clearance, embedding anticoagulants in the membrane, embedding renal proteins and/or renal tube cells into the membrane matrix to provide enhanced blood solute clearance better synthesized natural kidney function to the MECS dialyzer.

MECS dialyzers made in accordance with the present invention, provide embedded highly-parallel or perpendicular arrays of microchannels capable of accelerating the mass transfer in dialysis applications. Small characteristic sizes provided by the microchannels provide the benefits of large surface-to-volume ratios, laminar flow conditions and the opportunity of operating at elevated pressures.

Extremely high rates of mass transfer are obtainable in microchannels. The MECS dialyzer which incorporates microchannel geometry and micro-lamination manufacturing technologies radically reduces the characteristic or residence time required for mass transfer in a dialysis application. Unlike the conventional dialysis unit, the microtechnology-based design maintains micro-scale dimensions evenly on both sides of the membrane. Also, unlike conventional hollow-fiber dialyzers, microchannel geometry and microlamination technology allow for a much better and easier realization of an accurately engineered flow on both sides of the dialyzer membrane. In an embodiment in accordance with the present invention, for example, a microtechnology-based MECS dialyzer is provided with dialysate flow channel dimensions of 100 microns. Compared to a conventional dialyzer with hollow fibers, this geometry reduces the size of a dialyzer by a factor of 10 to 100 for the same operating parameters.

The MECS dialyzer is designed to maximize blood clearance with minimized membrane surface. The blood flow field is engineered to maximize blood clearance with minimum blood residence time within the dialyzer, to provide a minimum pressure drop across the membrane, and to minimize blood cell damage. The dialysate flow field is engineered to maximize the diffusion process with a minimum amount of dialysate Dialysis removes waste products, solute, from the blood by means of diffusion. The dialysate is only exposed to the membrane for a short time, so the solute molecules do not have sufficient time to diffuse evenly into a relatively large volume of dialysate and will develop a diffusion gradient if not optimized. Therefore, effective diffusion in dialysis only occurs nearest the membrane and decreases in effectiveness as the distance from the membrane increases.

A major benefit of the MECS dialyzer in accordance with the present invention is the ability to optimize the dialysate flow so as to approach 100% utilization. In standard hollow fiber dialyzers, for example, the gradient on the blood side is relatively controlled due to the relatively small diameter of the path of the blood in the fibers. But the gradient on the dialysate side is uncontrolled due to the relatively large flow path and volume of the dialysate. This inability to control the diffusion gradient on the dialysate side of the membrane leads to poor utilization of the dialysate fluid. Much of the dialysate that passes through the standard dialyzer is not exposed to the membrane and it leaves the dialyzer without being used to clean the blood.

By comparison, a MECS dialyzer in accordance with embodiments of the present invention, uses a structured flow of dialysate through fixed-width microchannels. The spacing of the microchannels is predetermined for effective utilization of the dialysate used to clean the blood. Less dialysate solute reduces the dialysis machine size.

Additionally, the structured flow path minimizes areas of stagnant flow, eliminates shunt flows, and ensures maximum utilization of all areas of membrane exposed to the dialysate flow. This greatly improves solute clearance and allows for the dialyzer to have less surface area for a given performance requirement as compared with currently available hollow fiber dialyzers. The reduced membrane length and surface area reduces the pressure on the blood leading to a reduction in hemolysis and reduction in the amount of blood within the circuit that is outside the patient during treatment.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A dialyzer comprising:
   a plurality of semipermeable membrane sheets, each of the semipermeable membrane sheets having a sheet first side and a sheet second side opposite the sheet first side and a sheet first end and a sheet second end opposite the sheet first end; and
   a plurality of flow separators, each flow separator being an elongated member, at least two flow separators depend from each of the sheet first side and sheet second side of each of the plurality of semipermeable membrane sheets, the at least two flow separators being spaced a predetermined distance apart and substantially parallel therewith, a sheet first side of one of the semipermeable membrane sheets being adjacent a sheet second side of another one of the semipermeable membrane sheets such that respective flow separators of adjacent semipermeable membrane sheets are in facing relationship and coupled together therefore defining coupled flow separators, wherein the plurality of semipermeable membrane sheets and coupled flow separators define alternating first microchannel layers comprising substantially parallel first microchannels and second microchannel layers comprising substantially parallel second microchannels, each first microchannel and each second microchannel being defined by two of the plurality of semipermeable membrane sheets, the first microchannels and second microchannels extending from each of the sheet first end to the sheet second end, the first microchannels and second microchannels being in fluid communication with each other via one of the plurality of semipermeable membrane sheets therebetween, the first microchannels operable for receiving a first fluid stream comprising blood and the second microchannels operable for receiving a second fluid stream comprising dialysate;

the dialyzer further comprising a first header and a second header, the first header comprising an inlet in fluid communication with the first microchannels at the sheet first end and an outlet in fluid communication with the second microchannels at the sheet first end, the second header comprising an inlet in fluid communication with the second microchannels at the sheet second end and an outlet in fluid communication with the first microchannels at the sheet second end.

2. The dialyzer of claim 1, wherein the first microchannels of each first microchannel layer are parallel therewith and the second microchannels of each second microchannel layer are parallel therewith.

3. The dialyzer of claim 2, wherein the first microchannels and second microchannels are parallel therewith.

4. The dialyzer of claim 2, wherein the first microchannels and second microchannels are orthogonal therewith.

5. A dialysis system, comprising:
   blood-handling apparatus;
   dialysate-handling apparatus; and
   a dialyzer, the dialyzer comprising a plurality of semipermeable membrane sheets, each of the semipermeable membrane sheets having a sheet first side and a sheet second side opposite the sheet first side and a sheet first end and a sheet second end opposite the sheet first end; and
   a plurality of flow separators, each flow separator being an elongated member, at least two flow separators depend from each of the sheet first side and sheet second side of each of the plurality of semipermeable membrane sheets, the at least two flow separators being spaced a predetermined distance apart and substantially parallel therewith, a sheet first side of one of the semipermeable membrane sheets being adjacent a sheet second side of another one of the semipermeable membrane sheets such that respective flow separators of adjacent semipermeable membrane sheets are in facing relationship and coupled together therefore defining coupled flow separators, wherein the plurality of semipermeable membrane sheets and coupled flow separators define alternating first microchannel layers comprising substantially parallel first microchannels and second microchannel layers comprising substantially parallel second microchannels, each first microchannel and each second microchannel being defined by two of the plurality of semipermeable membrane sheets, the first microchannels and second microchannels extending from each of the sheet first end to the sheet second end, the first microchannels and second microchannels being in fluid communication with each other via one of the plurality of semipermeable membrane sheets therebetween, the first microchannels operable for receiving a first fluid stream comprising blood and the second microchannels operable for receiving a second fluid stream comprising dialysate, the blood-handling apparatus being in fluid communication with the first microchannels, and the dialysate-handling apparatus being in fluid communication with the second microchannels.

6. The dialysis system of claim 5, the blood-handling apparatus operable to supply blood to the first microchannels at the sheet first end and withdraw blood from the first microchannels at the sheet second end, and the dialysate-handling apparatus operable to supply dialysate to the second microchannels at the sheet second end and withdraw dialysate from the second microchannels at the sheet first end wherein the flow of blood through the first microchannels is countercurrent to the flow of dialysate through the second microchannels.

7. The dialysis system of claim 5, the blood-handling apparatus operable to supply blood to the first microchannels at the sheet first end and withdraw blood from the first microchannels at the sheet second end, and the dialysate-handling apparatus operable to supply dialysate to the second microchannels at the sheet first end and withdraw dialysate from the second microchannels at the sheet second end wherein the flow of blood through the first microchannels is concurrent to the flow of dialysate through the second microchannels.

8. The dialysis system of claim 5 wherein the flow of blood through the first microchannels is non-turbulent.

9. The dialysis system of claim 5 wherein the flow of blood through the first microchannels is laminar.

10. The dialysis system of claim 5 wherein the flow of blood through the first microchannels is crosscurrent to the flow of dialysate through the second microchannels.

11. The dialysis system of claim 5 wherein the first and second microchannels have an internal dimension of up to 1000 microns.

12. The dialysis system of claim 5, wherein the first microchannels and second microchannels are parallel therewith.

13. The dialysis system of claim 5, wherein the first microchannels and second microchannels are orthogonal therewith.

14. The dialyzer of claim 1 being operable such that the first fluid stream that may be within the first microchannels is countercurrent to the second fluid stream that may be within the second microchannels.

15. The dialyzer of claim 1 being operable such that the first fluid stream that may be within the first microchannels is concurrent to the second fluid stream that may be within the second microchannels.

16. A dialyzer comprising:
a plurality of semipermeable membrane sheets, each of the semipermeable membrane sheets having a sheet first side and a sheet second side opposite the sheet first side and a sheet first end and a sheet second end opposite the sheet first end; and
a plurality of flow separators, each flow separator being an elongated member, at least two flow separators depend from each of the sheet first side and sheet second side of each of the plurality of semipermeable membrane sheets, the at least two flow separators being spaced a predetermined distance apart and substantially parallel therewith, a sheet first side of one of the semipermeable membrane sheets being adjacent a sheet second side of another one of the semipermeable membrane sheets such that respective flow separators of adjacent semipermeable membrane sheets are in facing relationship and coupled together therefore defining coupled flow separators, wherein the plurality of semipermeable membrane sheets and coupled flow separators define alternating first microchannel layers comprising substantially parallel first microchannels and second microchannel layers comprising substantially parallel second microchannels, each first microchannel and each second microchannel being defined by two of the plurality of semipermeable membrane sheets, the first microchannels and second microchannels extending from each of the sheet first end to the sheet second end, the first microchannels and second microchannels being in fluid communication with each other via one of the plurality of semipermeable membrane sheets therebetween, the first microchannels operable for receiving a first fluid stream comprising blood and the second microchannels operable for receiving a second fluid stream comprising dialysate;
the dialyzer further comprising a first header and a second header, the first header comprising a first inlet in fluid communication with the first microchannels at the sheet first end and a second inlet in fluid communication with the second microchannels at the sheet first end, the second header comprising a first outlet in fluid communication with the first microchannels at the sheet second end and a second outlet in fluid communication with the second microchannels at the sheet second end.

17. The dialyzer of claim 16 being operable such that the first fluid stream that may be within the first microchannels is countercurrent to the second fluid stream that may be within the second microchannels.

18. The dialyzer of claim 16 being operable such that the first fluid stream that may be within the first microchannels is concurrent to the second fluid stream that may be within the second microchannels.

* * * * *